US011631484B1

(12) United States Patent
Hanina et al.

(10) Patent No.: US 11,631,484 B1
(45) Date of Patent: Apr. 18, 2023

(54) METHOD AND APPARATUS FOR PREDICTING, ENCOURAGING, AND INTERVENING TO IMPROVE PATIENT MEDICATION ADHERENCE

(71) Applicant: AIC Innovations Group, Inc., New York, NY (US)

(72) Inventors: Adam Hanina, New York, NY (US); Jeff Galas, Amherst, NY (US)

(73) Assignee: AIC Innovations Group, Inc., New York, NY (US)

( * ) Notice: Subject to any disclaimer, the term of this patent is extended or adjusted under 35 U.S.C. 154(b) by 1156 days.

(21) Appl. No.: 14/517,468

(22) Filed: Oct. 17, 2014

Related U.S. Application Data

(60) Provisional application No. 61/893,711, filed on Oct. 21, 2013.

(51) Int. Cl.
*G06N 5/04* (2006.01)
*G16H 20/10* (2018.01)
*H04L 51/00* (2022.01)

(52) U.S. Cl.
CPC ............ *G16H 20/10* (2018.01); *G06N 5/04* (2013.01); *H04L 51/00* (2013.01)

(58) Field of Classification Search
CPC .......... G06N 5/04; G06N 5/02; G06N 99/005; G06N 20/00; G09B 7/04; G06F 9/4446
USPC .......................................................... 706/11
See application file for complete search history.

(56) References Cited

U.S. PATENT DOCUMENTS

| 7,359,214 B2 | 4/2008 | Heard |
| 7,761,311 B2* | 7/2010 | Clements ............... G16H 20/10 |
| | | 705/3 |
| 8,538,775 B2 | 9/2013 | Skomra |
| 8,666,781 B2 | 3/2014 | Hanina et al. |
| 9,183,601 B2 | 11/2015 | Hanina et al. |
| 9,293,060 B2 | 3/2016 | Hanina et al. |
| 10,691,776 B1* | 6/2020 | Tomala ................. G16H 50/70 |
| 2008/0050055 A1 | 2/2008 | Austreng et al. |

(Continued)

OTHER PUBLICATIONS

Ho et al., *Adherence to cardioprotective medications and mortality among patients with diabetes and ischemic heart disease* BMC Cardiovasc Disord. 15:6:48 (Dec. 2006).

(Continued)

*Primary Examiner* — Viker A Lamardo
(74) *Attorney, Agent, or Firm* — Fish & Richardson P.C.

(57) ABSTRACT

A system and method for predictively following up with a user to improve medication adherence. The system includes a medication adherence monitoring apparatus for determining whether a user has taken a medication at a predetermined medication administration time, and a processor for categorizing each determination of whether a user has taken the medication at a predetermined time across a plurality of different dimensions, combining the plurality of different dimensions in a plurality of different combinations to generate a patient adherence score across each of the plurality of different combinations, and ranking a user in accordance with each of the plurality of different combinations. The system further includes a communication apparatus for contacting a user to encourage medication adherence in accordance with at least the ranking of the user in accordance with one or more of the plurality of different combinations.

18 Claims, 4 Drawing Sheets

(56) References Cited

U.S. PATENT DOCUMENTS

| | | | | |
|---|---|---|---|---|
| 2009/0138251 | A1* | 5/2009 | Bugrim | G16B 50/00 703/11 |
| 2011/0004110 | A1* | 1/2011 | Shusterman | G16H 50/20 600/509 |
| 2011/0119073 | A1* | 5/2011 | Hanina | H04N 5/232941 705/2 |
| 2011/0153360 | A1* | 6/2011 | Hanina | G16H 10/20 705/3 |
| 2011/0153361 | A1* | 6/2011 | Hanina | G16H 20/00 705/3 |
| 2011/0231202 | A1* | 9/2011 | Hanina | G16H 40/67 705/2 |
| 2011/0275051 | A1* | 11/2011 | Hanina | G16H 20/10 434/365 |
| 2012/0009555 | A1* | 1/2012 | Hanina | G16H 40/63 434/262 |
| 2012/0075464 | A1* | 3/2012 | Derenne | H04N 7/185 348/135 |
| 2012/0179480 | A1* | 7/2012 | Patel | G16H 50/30 705/2 |
| 2012/0316897 | A1* | 12/2012 | Hanina | G16H 20/70 705/3 |
| 2013/0127620 | A1* | 5/2013 | Siebers | G06K 9/00302 340/573.1 |
| 2014/0052475 | A1* | 2/2014 | Madan | G06F 19/3437 705/3 |
| 2014/0365408 | A1* | 12/2014 | Snyder | G06F 19/00 706/12 |
| 2015/0262499 | A1* | 9/2015 | Wicka | G06Q 50/22 705/14.27 |

OTHER PUBLICATIONS

Kenreigh et al., *Medication Adherence: A Literature Review Medscape*, 2005.

Marder, Stepher R., *Overview of Partial Compliance*, J Clin Psychiatry 64(suppl 16)3-9 (2003).

McNabb et al., *Patterns of Adherence to Antiretroviral Medication, The Value of Electronic Monitoring*, AIDS, 17(12): 1763-767 (2003).

National Council on Patient Information & Education. *Thinking Outside the Pillbox A System-wide Approach to Improving Patient Medication Adherence for Chronic Disease*. NEHI Research Brief Aug. 2009. www.nehi.net/uploads/full_report/pa_issue_brief_final.pdf.

National Council on Patient Information and Education. *Enhancing Prescription Medicine Adherence*. A National Action Plan. Bethesda, Md. Aug. 2007. www.intelecare.com/downloads/ncpie-adherence-report.pdf.

Osterberg, et al., *Adherence to Medication*, New Engl J Med, 353:487-97 (2005).

Simmons et al., *Unpredictability of deception in compliance with physician-prescribed bronchodilator inhaler use in a clinical trial*, Chest 118:290-295 (2000).

Sokol et al., *Impact of medication adherence on hospitalization risk and healthcare cost*, Med Care. 43(6):521-30 (Jun. 2005).

The Trend Report Series, 2008 Patient Adherence Update: New Approaches for Success, Oct. 2008 (17 pages).

Friedman et al., "Doctor-patient communication, health-related beliefs, and adherence in glaucoma results from the Glaucoma Adherence and Persistency Study," Ophthalmology, Aug. 2008, 115(8):1320-1327.e3.

Friedman et al., "Risk factors for poor adherence to eyedrops in electronically monitored patients with glaucoma," Ophthalmology, Jun. 2009, 116(6):1097-1105.

Gellad et al., "A Review of Barriers to Medication Adherence: A Framework for Driving Policy Options," RAND, 2009, 68 pages.

Stop TB Partnership, "Actions for life: towards a world free of tuberculosis," The Global Plan to Stop TB 2006-2015, 2006, retrieved from URL <http://whqlibdoc.who.int/publications/2006/9241593997_eng.pdf>, 172 pages.

Voils et al., "Social support and locus of control as predictors of adherence to antidepressant medication in an elderly population," Am J Geriatr Psychiatry, Feb. 2005, 13(2)457-165.

Wu et al., "Predictors of medication adherence using a multidimensional adherence model in patients with heart failure," J Card Fail, Sep. 2008, 14(7):603-614.

Wu et al., "Testing the psychometric properties of the Medication Adherence Scale in patients with heart failure," Heart & Lung, Sep.-Oct. 2008, 37(5):334-343.

\* cited by examiner

METHOD AND APPARATUS FOR PREDICTING, ENCOURAGING, AND INTERVENING TO IMPROVE PATIENT MEDICATION ADHERENCE

CROSS REFERENCE TO RELATED APPLICATIONS

This application claim the benefit of U.S. Provisional Patent Application Ser. No. 61/893,711, titled "Method and Apparatus for Predicting, Encouraging, and Intervening to Improve Patient Medication Adherence", filed Oct. 21, 2013 to Hanina et al., the contents thereof being incorporated herein by reference.

This invention was made with government support under grant number 9R44TR000873-02 awarded by National Center for Advancing Translational Sciences, National Institutes of Health. The Government has certain rights in the invention.

TECHNICAL FIELD

This application relates generally to monitoring of patient medication adherence and more specifically to the collection of patient adherence data to profile the patient, prediction of potential future non-adherence patients, and intervention with those patients before they become chronically non-adherent.

BACKGROUND

The total healthcare cost of drug-related morbidity, including poor adherence, is estimated at $290 billion per year in the US. "National Council on Patient Information & Education. Thinking Outside the Pillbox A System-wide Approach to Improving Patient Medication Adherence for Chronic Disease. NEHI Research Brief. August 2009. www.nehi.net/uploads/full_report/pa_issue_brief_final.pdf." Treatment of patients with poor adherence can require twice the resources from the healthcare system than treatment of more compliant individuals. "Sokol M, McGuigan K, Verbrugge R, Epstein R. Impact of medication adherence on hospitalization risk and healthcare cost. Med Care. June, 2005; 43(6):521-30." Mortality and morbidity rates are much higher for patients who do not follow their prescribed drug therapy, especially for patients suffering from a chronic illness. "Ho P, Magid D, Masoudi F, McClure D, Rumsfeld J. Adherence to cardioprotective medications and mortality among patients with diabetes and ischemic heart disease. BMC Cardiovasc Disord. December, 2006; 15; 6:48." Currently, 75% of healthcare spending in the US is directed towards treatment of chronic disease. "CDC. Chronic Disease Prevention and Health Promotion. http://www.cdc.gov/chronicdisease/resources/publications/AAG/chronic.htm." These same chronically ill patients who are also nonadherent to their medication prescriptions are twice as likely to be hospitalized. "Kenreigh C, Wagner L. Medication Adherence: A Literature Review 2005. Medscape. 2005. http://www.medscape.com/viewarticle/514164"; and "Sokol M, McGuigan K, Verbrugge R, Epstein R. Impact of medication adherence on hospitalization risk and healthcare cost. Med Care. June, 2005; 43(6):521-30." In psychiatric patients in particular, medication nonadherence is among the most common causes of psychotic relapse and rehospitalization. "Marder, Stepher R., Overview of Partial Compliance, J Clin Psychiatry 2003; 64[suppl 16]; 3-9."

Barriers to medication adherence such as the perceived impact of a medicine, knowledge about illness, forgetfulness, or lack of social support, "Friedman et. al.; Voila et al.; Wu et al. Three studies quoted in W. F., Grenard J, McGlynn E. A. A Review of Barriers to Medication Adherence: A Framework for Driving Policy Options. RAND, 2009", help to explain why 75% of Americans do not take their medicine as prescribed. "National Council on Patient Information and Education. Enhancing Prescription Medicine Adherence: A National Action Plan. Bethesda, Md. August, 2007. www.intelecare.com/downloads/ncpie-adherence-report.pdf." Traditional monitoring methods have problems with reliability and cost and generally fail to allow for immediate intervention by a healthcare professional. Pill counting and patient interviews are unreliable ways of measuring medication adherence. "Osterberg L, Blaschke T. Adherence to medication. N Engl J Med. Aug. 4, 2005; 353(5):487-497." Self-reporting by individuals, using ePRO diaries, IVRS or web portal communications have also been shown to be untrustworthy as many patients fail to record accurate data. "Simmons M, Nides M, Rand C, Wise R, Tashkin D. Unpredictability of deception in compliance with physician-prescribed bronchodilator inhaler use in a clinical trial. Chest 2000 118:290-295." Technology such as digital pill container caps and smart packaging report only when patients open the medication container and cannot confirm medication administration. Importantly, these methods do not provide timely information sufficient to support care provider intervention. Smart pills, while accurate, are expensive and require the manufacturing process of the medication to be altered to include an RFID or other identification computer chip therein. Even data tools such as electronic health records fail to capture patient behavior such as medication adherence rates despite a new emphasis on meaningful use, fail to perform any useful analysis on captured data, and fail to learn any behavioral patterns to assist in adherence monitoring. "National Cancer Institute. https://www.gem-beta.org/Public/EHRInitiative.aspx?cat=4."

An extremely effective way to confirm medication adherence is through direct observation, i.e. watching a patient take their medication. The WHO's Directly Observed Treatment, short course (DOTs) program has radically improved compliance rates of TB patients. "Stop TB Partnership. The Global Plan to Stop TB, 2006-2015: Actions for life: towards a world free of tuberculosis. Geneva: WHO; 2006. http://whqlibdoc.who.int/publications/2006/9241593997_eng.pdf." Such direct observation is typically employed in phase 1 clinical trials, where assurance of adherence is critical. Unfortunately, the labor-intensive nature of the program is expensive, time consuming and geographically limited, as well as being inconvenient and burdensome to patients.

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series, 2008 Patient Adherence Update:*

New Approaches for Success, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication.

Traditionally, participants attend introductions and follow ups for clinical trials in-person. Other patients attempting to adhere to a particular medication protocol similarly are given a prescription and a particular set of instructions from a prescribing medical provider or prescribing doctor, and then compliance is measured, typically by counting remaining pills, at a next visit with that prescribing professional. Thus, data collection is similarly limited to patient visits, rather than on a daily basis. Old methods such as patient questioning and pill counting have been proven to be inadequate measures of adherence and offer no information on dose timing and drug holidays (omission of medication for three or more sequential days, for example).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement. Further, electronic patient diaries allow for ease of entry of data by a patient. These diaries, however, are still subject to issues related to compliance with medication adherence. Thus, even if a patient is meticulous about entering information into the diary, and thus complying with the requirements for data entry, there is still no guarantee that they are properly taking medication at prescribed times.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp1, 763-767, October 2003. Furthermore, it is well known that it is expensive to check up on people and directly monitor medication administration, but studies have shown that care provider intervention has a significant benefit on medication adherence rates and patient behavior. http://www.ahdbonline.com/feature/engaging-providers-medication-adherence-health-plan-case-study. To date, technologies alone have only been used in an attempt to monitor compliance rather than to encourage it. Furthermore, there has been no comprehensive system provided that allows for the management of multiple patients and multiple patient populations. While current technology may allow poor compliers to be recognized, as will be described below, the proposed apparatus and method of the present invention will help to encourage pharmaceutical compliance and tackle some of the problems that are encountered in the clinical trial process in particular, and the medication protocol monitoring problem in general.

A number of systems exist that provide instructions to a user regarding when to take a medication and records when the user indicates that a medication has been taken. U.S. Pat. No. 7,359,214 describes such a system. A device is provided that instructs a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials and other active patient monitoring of medication adherence.

Most importantly, this system provides no mechanism for actually confirming that a patient is in fact ingesting or otherwise properly administering medication as required in a clinical drug trial, or as prescribed by a prescribing physician in the case where adherence to a particular regimen may prove to be critical to efficacy of the prescription regimen. Further, while the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Additionally, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Still further, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Additionally, there is no method for determining in near real time whether a patient has taken their medication, and does not allow for intervention on the part of a healthcare provider to immediately address adherence issues. Finally, this system is expensive and requires constant maintenance to confirm that the various mechanical parts are in working order.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence (i.e. taking of the medication by a particular person) or the relationship of adherence to the efficacy of the drug over time. Furthermore, the system relies only on a single still image of the medication, thus not being very versatile if the image is poor, and also cannot confirm completion of an activity of administration. When requiring adherence to a predetermined protocol for a clinical trial, this is particularly relevant. Additionally, monitoring medication adherence of higher risk populations, or a particular medication administration protocol that requires a number of sequential steps is not possible with a system that employs a single image.

Additionally, existing systems fail to maintain an audit trail for post administration review by a medical official or other clinical trial administrator, and further cannot therefore confirm confirmation of proper medication administration. They also fail to allow for intervention by a healthcare provider on a near real time basis, and indeed fail to properly allow an administrator to monitor a large group of patients efficiently and accurately. They additionally fail to provide a predictive mechanism for determining future potential non-adherence among patients.

Therefore, it would be desirable to provide a method and apparatus that overcome the drawbacks of the prior art.

SUMMARY

In U.S. patent application Ser. No. 12/620,686 filed Nov. 18, 2009 titled Method and Apparatus for Verification of Medication Administration Adherence (published as US Patent Application Publication No. 2011/0119073); Ser. No. 12/646,383 filed Dec. 23, 2009 titled Method and Apparatus for Verification of Clinical Trial Adherence (published as US Patent Application Publication No. 2011/0153360); Ser. No. 12/646,603 filed Dec. 23, 2009 titled Method and Apparatus for Management of Clinical Trials (issued as U.S. Pat. No. 8,666,781); Ser. No. 12/728,721 filed Mar. 22, 2010 titled Apparatus and Method for Collection of Protocol Adherence Data (issued as U.S. Pat. No. 9,183,601); Ser. No. 12/815,037 filed Jun. 14, 2010 titled Apparatus and Method for Recognition of Patient Activities When Obtaining Protocol Adherence Data (issued as U.S. Pat. No. 9,293,060); Ser. No. 13/189,518 filed Jul. 24, 2012 titled Method and Apparatus for Monitoring Medication Adherence (published as US Patent Application Publication No. 2012/0316897); and Ser. No. 13/235,387 filed Sep. 18, 2011 titled Apparatus and Method for Recognition of Patient Activities (issued as U.S. Pat. No. 9,875,666), the entire contents of each of these applications being incorporated herein by reference, as well as in other co-owned applications, the inventors of the present invention have proposed a system and method that allow for complete control and verification of adherence to a prescribed medication protocol or machine or apparatus use in a clinical trial or other setting, whether in a health care provider's care, or when self administered in a homecare situation by a patient. As part of these applications, determination of when a user has taken a pill is an important step in the monitoring process. Further determination of user administration of inhalable, injectable and other medication administration processes may also be provided. These applications also describe a dashboard presented to one or more healthcare providers in order to properly aggregate and review various monitored medication administration sequences for any number of patients.

These applications present the only medication management system that may determine whether a user is actually following a protocol (preferably employing audio/video analysis of captured audio/video information), provide additional assistance to a user, starting with instructions, video instructions, audio instructions, avatar based instructions and the like, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings.

Thus, in accordance with various embodiments of the invention, it may be determined whether the correct patient is taking the correct medication at the correct time. It is therefore also contemplated in accordance with one or more embodiments of the present invention that upon determination of a failure or expected future failure of medication adherence, intervention may be provided to the patient. The inventors of the present invention have discovered that while all monitoring systems have limitations, one which is rarely cited is the lack of a combined monitoring and intervention system. Yet feedback to patients of their detailed dosing histories over time is essential to managing their adherence. Most interventions have lacked the necessary complexity to be effective and most are difficult to assess given the poor monitoring methods utilized in the study designs. Examples of electronic-based interventions using text messages, electronic reminders, or online education information also show mixed results. Interventions must be multi-faceted and continuously reinforced over time.

Therefore, in accordance with one or more embodiments of the present invention, a device for gathering adherence data, such as one or more devices or apparatuses described in one or more of the applications incorporated herein by reference, or any other medication adherence monitoring apparatus, such as an interactive mirror, mobile device and the like may be provided. In addition to gathering such adherence data, other data may also preferably be captured. While the system may be employed for any patient population, a population for which maintaining adherence is important may be most desirable for use of the system. The population may be part of a clinical trial, or may be under the care of a provider or payer. For each dose, the device records if patients have taken their medication. All past adherence data is recorded by the device, allowing for intervention in case of a patient's non-adherence.

The inventors of the present invention have determined that when employing such an adherence monitoring device, it may not be desirable to contact each patient each time they miss a dose of medication. In particular, this will not be possible with large populations, and indeed may cause some backlash amongst the patients. At any given time, only some portion of patients will be having a problem taking their medication. Also, if there is a pattern to a patient's nonadherence, anticipating the missed or late doses and intervening proactively is preferable to intervening retrospectively after a dose has been missed. A proactive intervention has the chance of preventing a potentially missed dose, while a retrospective intervention addresses something that has already happened and cannot be changed.

It's also likely that the group of problematic patients will change over time. Throughout the course of treatment, there may be changes in a patient's adherence behavior. Factors that influence whether a patient takes his or her medication include: symptoms may come and go; side effects may come and go; changes in physical or mental health; changes in daily life (new job, etc.); fatigue with the medication-taking process; an intentional decision to stop taking the medication. It is desirable to understand when a change occurs, and to adjust monitoring and intervention accordingly. Not only is the method and apparatus presented in accordance with the present invention able to predict future behavior, but is also able to provide a classification system to identify urgency and priority related to a particular patient or group of patients. A recommendation system is also preferably provided to advise one of the most appropriate and effective intervention (from many) ranging from automated communications, psychoeducation, incentive structures etc. After application of such intervention is provided a determination of the effectiveness of the intervention may be determined, and this information may be further used to aid in selecting a future intervention.

Consider a patient who misses a dose every Saturday, but takes his dose every other day of the week, or uses a less reliable method of adherence confirmation, such as self reporting, on such a regular basis. A phone call to this patient each Sunday does not seem like a good use of resources, and it is questionable whether this will be effective in reminding him to take his medication six days later. While this behavior continues, perhaps in accordance with an embodiment of the present invention, the patient should get an automatic text message or other reminder every Friday, which anticipates the missed dose and does not use any additional resources. If at some point this patient begins randomly missing two or more doses per week, the text message may be discontinued and another intervention employed. Possible interventions include—but certainly aren't limited to—a phone call; educational information about the medication that reminds the patient why taking the medication regularly is important; questionnaires about the presence of side effects, symptoms, or any changes in the patient's daily life; or a suggestion to change the time of day at which the patient is scheduled to take the medication. Other information may be included to aid in profiling the patient and determining appropriate responses and interventions. Such information may include historical data, socioeconomic data, patient population type, disease state, etc. Such information may also be employed to generate a risk profile of a patient or patient population to determine one or more triggers for determining when a patient is at risk, and to which interventions the patient might best respond.

For all but the smallest patient populations, the inventors of the present invention have further recognized that the personnel responsible for overseeing such a patient population will not be able to get to know the characteristics of each individual patient. The question then arises as to which subset of patients should be brought to the attention of the personnel involved in managing the population. The patients who should get increased monitoring over the next k days are those at most risk for exhibiting poor adherence patterns over the next k days. The problem then becomes how to find this group of patients in the population. It would be ideal not to retrospectively identify the patients who have shown certain adherence patterns in the past, but to proactively identify those who are at risk of exhibiting those patterns in the near future, in accordance with one or more embodiments of the present invention.

The proposed invention preferably provides an automated system that optimizes monitoring and aids in making decisions about how and when to intervene with a patient, in accordance with one or more embodiments of the present invention. It is a data-driven system that preferably comprises two main modules that use the data collected from the adherence monitoring device to (1) summarize a patient's characteristics by computing a patient score (based on past behavior), and (2) identify patients who are likely to have an adherence rate below a certain level over some future time period by forecasting which upcoming doses, if any, a patient will miss. The system in accordance with one or more embodiments of the invention may also utilize a machine learning algorithm to profile patients with various electronic monitoring and behavior-based mechanisms (prescription refills, text reports, etc), and including one or more of the automated monitoring systems noted above. The system may also employ different methods for reporting adherence, such as automated determinations, self reporting, suspicious reporting, usability errors or other issues, location of the patient, demographics, and any other basis for categorization of the patient that may provide information as to the risk and need for urgency in an intervention.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

The detailed embodiments of the invention will now be described making reference to the following drawings in which like reference numbers denote like structure or steps.

Figure 1:
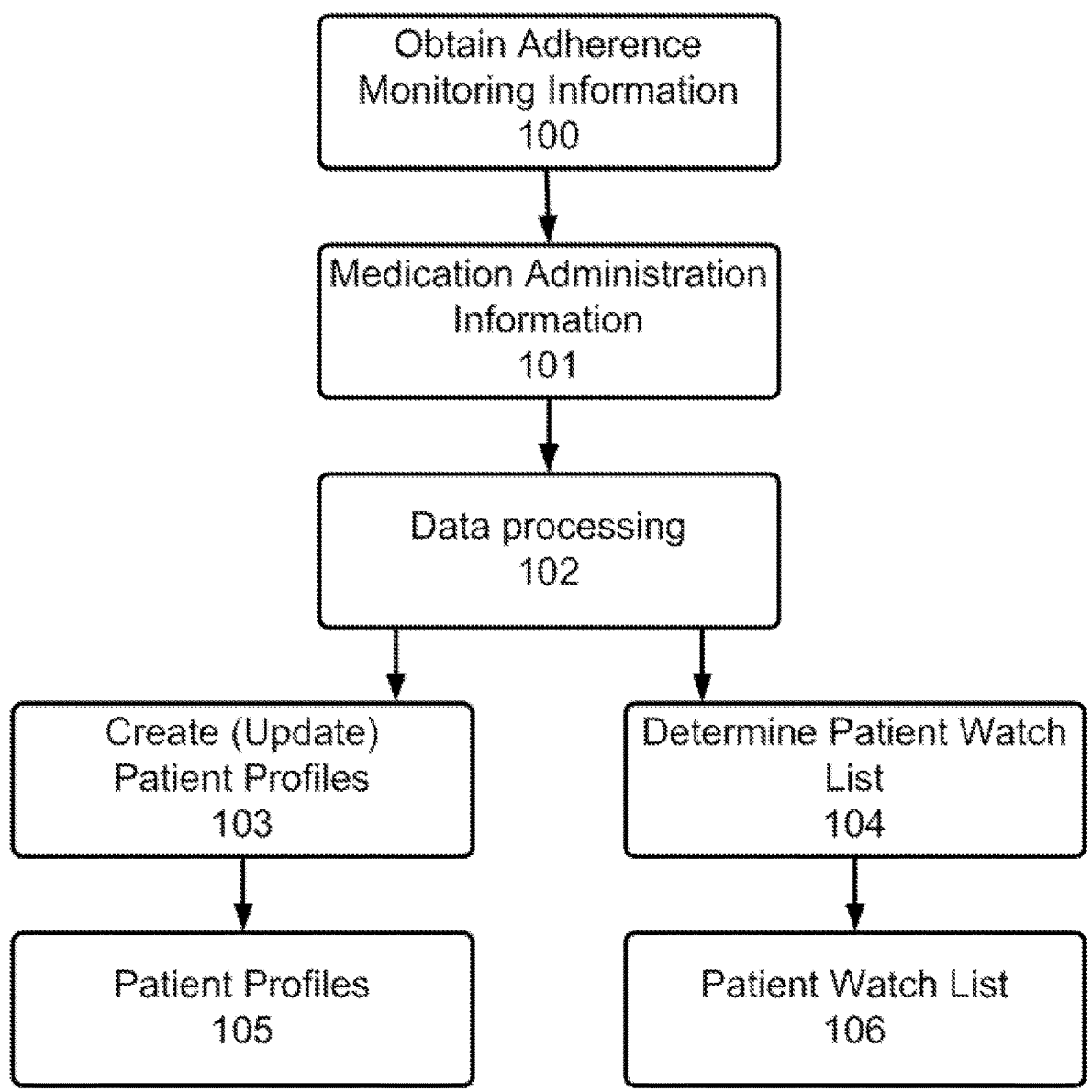
FIG. 1 is a flowchart diagram depicting an overall functioning of a system and method for identification of and predictive targeted interaction with one or more patients who may become non-adherence to a medication protocol, in accordance with one or more embodiments of the invention.

Referring first to FIG. 1, FIG. 1 shows a system for automatically identifying patients for proactive, targeted intervention. Patients are preferably enrolled in a medication monitoring program that obtains adherence monitoring information employing a medication adherence monitoring apparatus, such as one or more of the devices, apparatuses or systems noted above in the applications incorporated by reference herein. For example, the medication adherence monitoring apparatus is an apparatus that facilitates information presentation to a patient, information capture of medication administration at home in a homecare setting, in a hospital setting, in a clinical trial setting, or in any other setting in which medication adherence is potentially an issue, and other aspects described as part of the method and system of the pending applications noted above. Therefore, in accordance with the present invention, a video capture device is provided including a memory for storing captured video and other patient data, analyzing such captured data, transmitting such captured data to a remote location, receiving information from a remote location and providing information to the patient as preferred in accordance with the present invention. In accordance with a preferred embodiment of the invention, an apparatus is provided comprising a video capture device, an audio capture device, memory for storing such captured data, a processor adapted to operate analysis software for analyzing the captured data, a transmitter for transmitting the captured data, or other versions of the data or analysis results to a remote location, for receiving data and further instructions or communication from the remote location, and a display for providing such data or further instructions to the patient. Such apparatus may preferably interface with management software adapted to manage multiple patients, and thereby providing a full monitoring and data collection procedure. Each such medication adherence monitoring apparatus therefore preferably gathers medication adherence data on each medication administration event for each patient at step 100. The data may then be sent to a processing/analysis unit for processing at step 102. Processing/analysis unit may comprise a general purpose computing apparatus, and preferably includes one or more processors, non-transitory computer readable storage media, one or more input and/or/output devices. The system may be located on a local network, or in a remote location accessed through the Internet or other network, and may be provided as a cloud based computing system. The processing/analysis unit preferably performs two significant tasks in accordance with the various embodiments of the invention. At step 103, one or more patient scores to be employed in one or more patient profiles 105 are preferably created. In particular, the processing/analysis unit is configured to categorize each determination of whether a user has taken the medication at a predetermined time across a plurality of different dimensions, combine the plurality of different dimensions in a plurality of different combinations to generate a patient adherence score across each of the plurality of different combinations, and rank a user in accordance with each of the plurality of different combinations. In an ongoing patient monitoring system, step 103 may also be employed to update an existing patient score to be employed in an updated patient profile 105. At step 104, the processing/analysis unit may further determine a "watch list" of patients 106 who may require proactive intervention because they are at increased risk of non-adherence in the near future, and may also include one or more attributes from the patient profile 105 to make such a determination. A care provider may also manually place a patient on the watch list for any desired reason. Employing the watch list 106 in conjunction with the updated patient profiles 105, at step 107 a decision for whether, when, and how to intervene with a patient is preferably made. Alternatively or in addition, the display of the medication adherence monitoring apparatus may be configured to display one or more visualizations that show trends of the patient scores over time and to encourage medication adherence in accordance with at least the ranking of the user in accordance with one or more of the plurality of different combinations.

Figure 2:
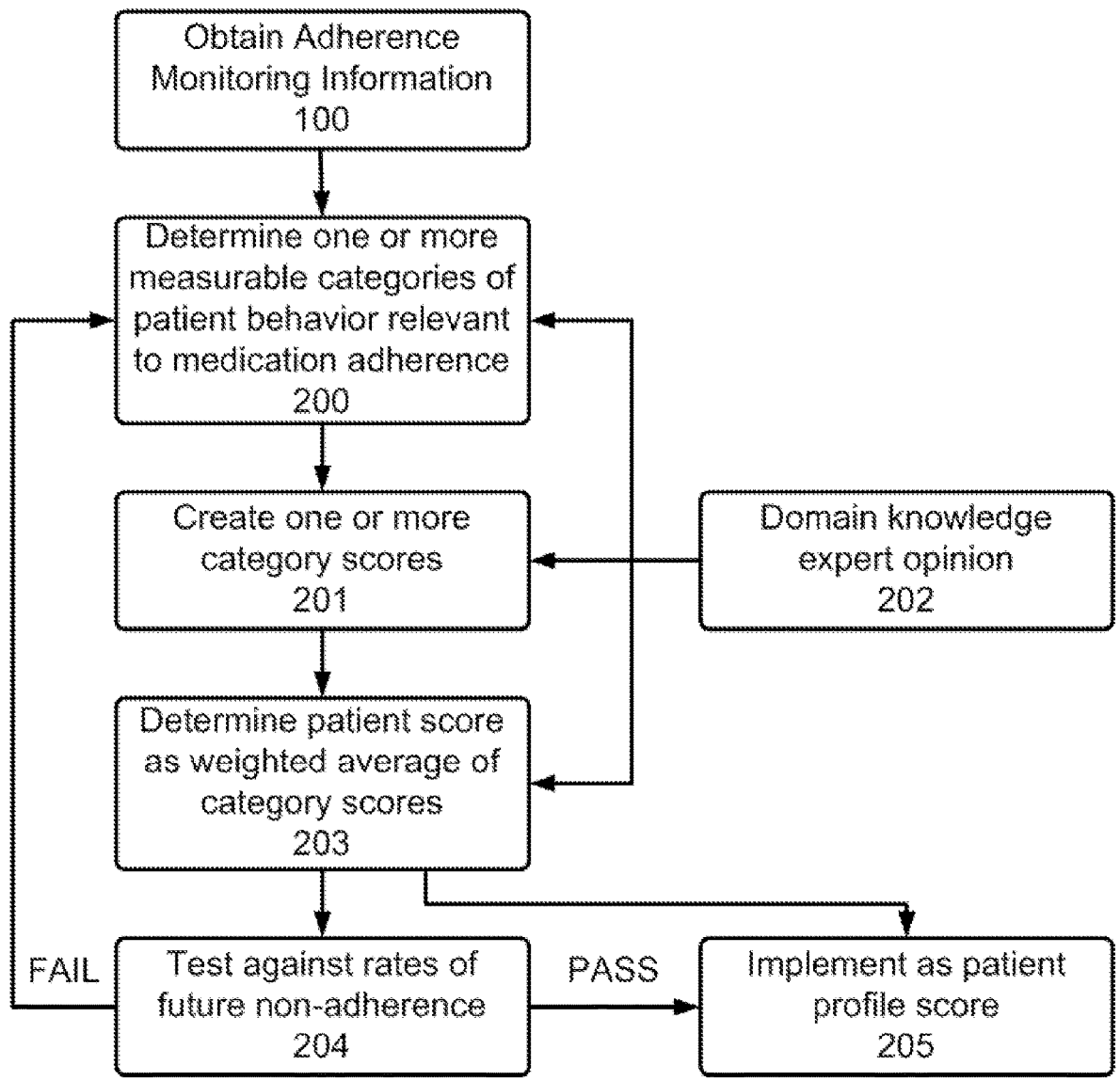
FIG. 2 is a flowchart diagram for creating a patient score in accordance with an embodiment of the invention.

Step 103, creating or updating patient profiles 105 preferably in accordance with one or more preferred embodiments of the present invention, makes use of a patient score, which preferably summarizes past patient behavior in a single number, multiple or a set of numbers, or other appropriate indicator, and which can be updated as often as after each dose of medication or on any other convenient time schedule. The patient profile 105 preferably is based at least upon a consideration of one or more of adherence, usability, suspiciousness, intervention responsiveness, and other historical data from the current or any other group of prior patients. FIG. 2 is a flow chart depicting a preferred method for creating a patient score in accordance with an embodiment of the invention. As noted with respect to FIG. 1, medication adherence information 101 and other patient data, as desired, may be obtained by a medication adherence monitoring apparatus at step 100. Different devices will likely collect different types and volumes of data, and will thus provide unique attributes on which to base a patient score or other indicator of historical or future patient performance. With the help of a domain knowledge expert 202 (or other store of knowledge, either automated, individual or the like) one or more categories of patient behavior that may be relevant to adherence are determined at step 200. Such categories may be determined in accordance with an expert opinion, or upon analysis of historical adherence correlation data with any number of possible categories of patient behavior.

A score is then preferably created for each category for each patient for each indicated category at step 201. These category scores summarize a patient's behavior in each category in single number or other desirable indicator. The patient score is then set equal to a weighted average or other desired combination of the category scores in step 203. The weighted average may also be determined in accordance with the automated or individual expert knowledge opinion, and may preferably be further determined in accordance with analysis of historical patient adherence data to determine which weightings provide a best fit to the available historical data. Therefore, as noted above, in addition to determining the categories along which to score a patient, the domain knowledge expert 202 (either automated or individual) may aid in determining data that is preferably used to compute each category score at step 200, determining how the data are combined to form each category score at step 201 and picking the weights or other interrelationship between the category scores that are used to create the formula for the overall patient score at step 203. As also noted above, this expert opinion may comprise an automated historical data analysis system providing one or more optimized set of categories and weightings. This score may be implemented at step 205. Optionally, at step 204 certain historical data may be selected to set the categories, scores and weights, and other historical data may be used to test the system. If the generated patient scores are properly predictive of non-adherence in the other historical data, then these parameters may be used to implement and determine one or more patient scores at step 205. If at step 204 the scores are found not to be indicative of future rates of adherence, as preferably determined by comparison of the scores to one or more additional patients, or one or more time frames from one or more patients not included in the data used to initially generate the scores, processing may return to step 200 where additional or different categories of patient behavior may be employed to generate one or more patient scores.

As described up until now, the patient score is not necessarily based on a predictive model and does not require obtaining any sample data, or on the population reaching a certain size, in order for patient scores to be computed (although, as described above, pseudo prediction may be employed to determine whether the patient scores may be considered predictive of future non-adherence in one or more patients). The intent of the patient score is to succinctly summarize a patient's past behavior. Thus, even at the beginning of a new monitoring program patient scores may be computed from day one.

Since the patient score is not necessarily based on a predictive model, it is not directly linked to the probability of a patient's future non-adherence. However, as noted above, the patient score can optionally be tested against future non-adherence at step 204 so that scores are correlated with non-adherence over some future time period. In this way, the patient score may be used to make predictions about patients' future adherence. If the test reveals that the patient score is acceptable as a predictor of non-adherence, then it may be implemented in step 205 as the basis for the patient profile, as noted above. Thus, a predictive model may be employed in order to predict potential future non-adherence.

It should also be noted that it is contemplated in accordance with one or more embodiments of the invention that several sets of weights may be chosen, thus creating several different patient scores based on the same category scores. In this case, each different patient score would, by design, emphasize different aspects of patient behavior. This may be desirable for providing different sores to a particular healthcare provider, or providing different patient scores to different healthcare providers, such as different scores to a nurse, doctor, family member, insurance company, and the like.

Figure 3:
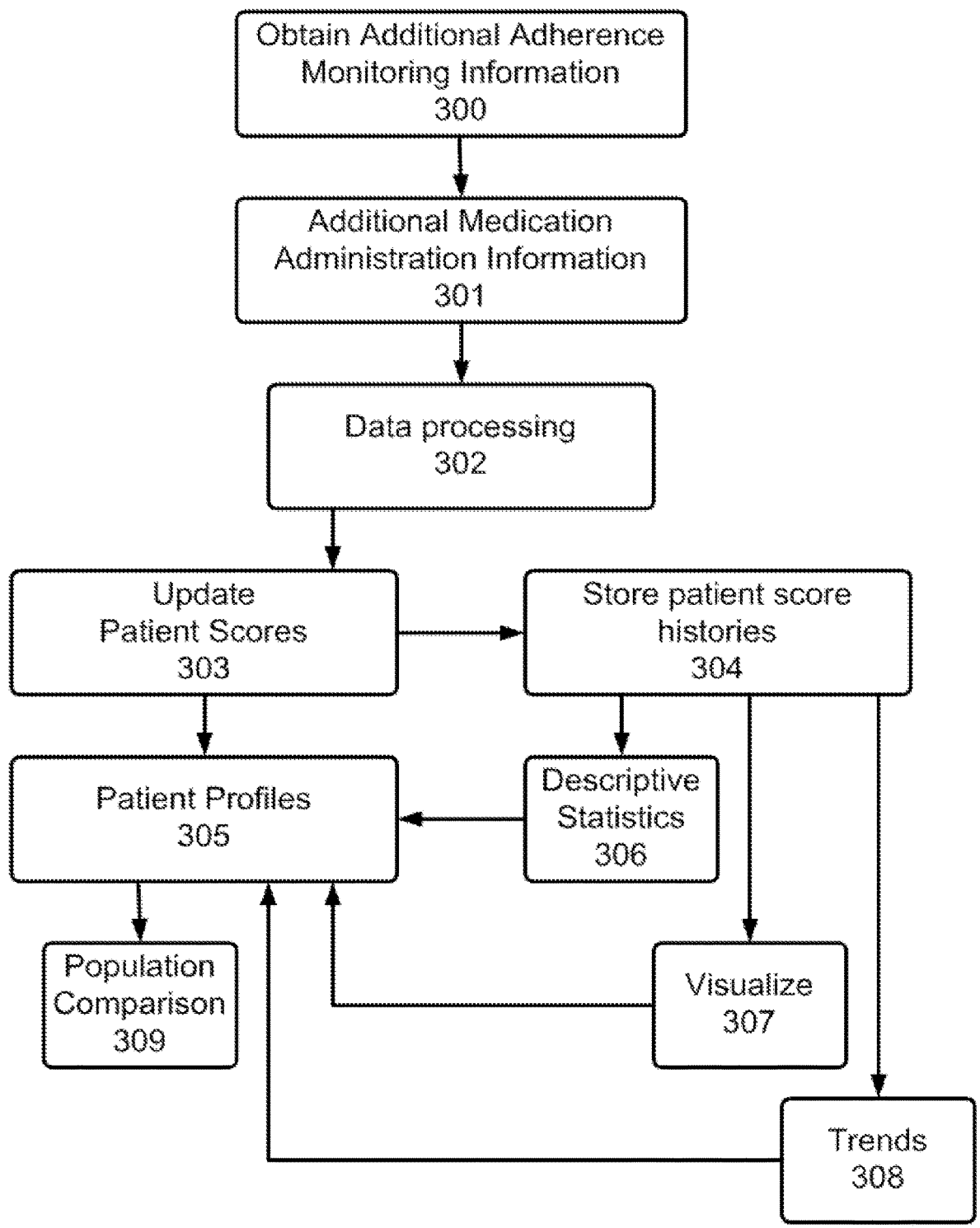
FIG. 3 is a flowchart depicting a method for creating and updating one or more patient profiles in accordance with an embodiment of the invention.

FIG. 3 depicts a method in accordance with an embodiment of the invention for updating one or more patient profiles. As is shown in FIG. 3, new additional medication administration information 301 may be collected at step 300 by the medication adherence monitoring apparatus. This additional information may be preferably employed to recompute one or more particular patient scores. Thus, at step 302, various data processing may be preformed to update one or more patient scores at step 303, which may then be employed to update one or more patient profiles at step 305. Furthermore, because patient scores can be computed as often as after each new dose, patient score histories are preferably established for each patient during the course of treatment at step 304. It should be noted that any processing that may be performed on one or more updated patient scores 303 and/or updated patient profiles 305 may also be performed on the initially created patient scores 103 and patient profiles 105. It is further contemplated in accordance with one or more embodiments of the present invention that the score system may be automatically and manually reviewed to grade content or events that have an impact on the score. For example, if one or more triggers are met and the system recommends an action to be taken (intervene with patient, retrain patient, retrain study coordinator, if persistent issue amongst other patients, increase level of guidance, increase incentives etc.) then the system may automatically watch for the impact and change on patient behavior in response to the intervention. Positive response may increase the use of such intervention while a negative response may result in less frequent use of the intervention. Manual scoring of the effectiveness of the intervention may also impact its future use.

Any number of desired descriptive statistics 306 may be determined from one or more of the updated and historical patient scores. Thus, the mean, standard deviation, median, range, quartiles, and the like, derived from one or more patient score histories 304, preferably may serve as the basis for updating one or more patient profiles at step 305. These values may be determined for patients overall, or within one or more smaller groups. For example, patients whose score histories have a narrow range—whether that range is toward the higher or lower end of the possible values of the score—could be considered "consistent," while patients whose score histories occur over wider ranges may be considered "inconsistent." Also, the mean taken over a patient's recent score history could be used to characterize the patient's behavior in the short term, while the mean taken over the patient's entire score history could be used to summarize the patient's long-term behavior. Patients landing in the top or bottom groups, even if not in those groups in their own sub-population, may still be subject to intervention as desired.

Patient score histories are also easily graphed at step 307 to provide one or more visualizations that readily show trends over time. Displaying these visualizations as part of the updated patient profile 305 may provide one or more healthcare providers managing the patient or patient population an immediate sense of the patient's behavior over time, and thus can aid in making judgments about whether and how to intervene with a patient. In addition to graphs against time, histograms, box plots, and other visualizations may be used that convey information about the distribution of patient scores for each patient.

Statistical analyses may also be performed on an individual patient's score history to compute one or more trends at step 308. For example, moving averages or other trending information may be computed in order to reveal and quantify short-term and long-term trends. Any adverse trends that are discovered may be preferably noted in the updated patient profile 305. Notifications may also be sent to the personnel managing the population in cases where adverse trends were discovered.

In addition to comparing various historical patient information, patient scores and histories may also be compared across one or more patient populations or sub-populations at step 309. Together with a collection of patient scores for any number of patients in a population or sub population, an individual's updated patient score 303 may be used to rank the patient relative to others in the population, thus giving a sense of the patient's performance relative to the rest of the population. The patient's rank is preferably indicated in the updated patient profile 305. It may be preferable to rank patients based on longer-term moving average of patient scores, so that rankings reflect longer-term behavior—and thus fluctuate less—rather than short-term behavior. Patient scores may also be aggregated across care providers, institutions, health care systems, etc. to give a profile of adherence of all or some patients associate with a particular institution or provider, etc. This information may also be helpful to provide a snapshot or patient and provider participation with the system.

Since at any given time the population mean and standard deviation can be computed using the population data in step 309, it can be determined whether a patient is an outlier relative to the rest of population, or has any other desired characteristic relative to the rest of the population. If the patient is an outlier, this may be noted in the updated patient profile 305. Also, it may be desirable to indicate in the updated patient profile 305 for what percentage of time a patient has been in the bottom, middle, or top x % of patients, for example using the automated monitoring system, indicating a self reported medication administration, etc.

As will be described below, in order to construct a watch list, non-adherence predictions for the future adherence of all patients in the population. Even if the patient is not added to the watch list, one or more predictive details may be integrated into the updated patient profile 305.

The paragraphs above describe examples of how patient scores can be used to construct patient profiles 105 and updated patient profiles 305 that numerically and visually summarize patient behavior. These patient profiles can be quickly read and understood and thus can aid in decision making regarding monitoring and intervention. It should also be noted that the analyses and visualizations that can be performed with the patient score can also be applied to category scores, and thus can be used to summarize patient behavior along any single dimension. In some cases, it may be desirable to integrate these category analyses and visualizations into the patient profile (105).

Figure 4:
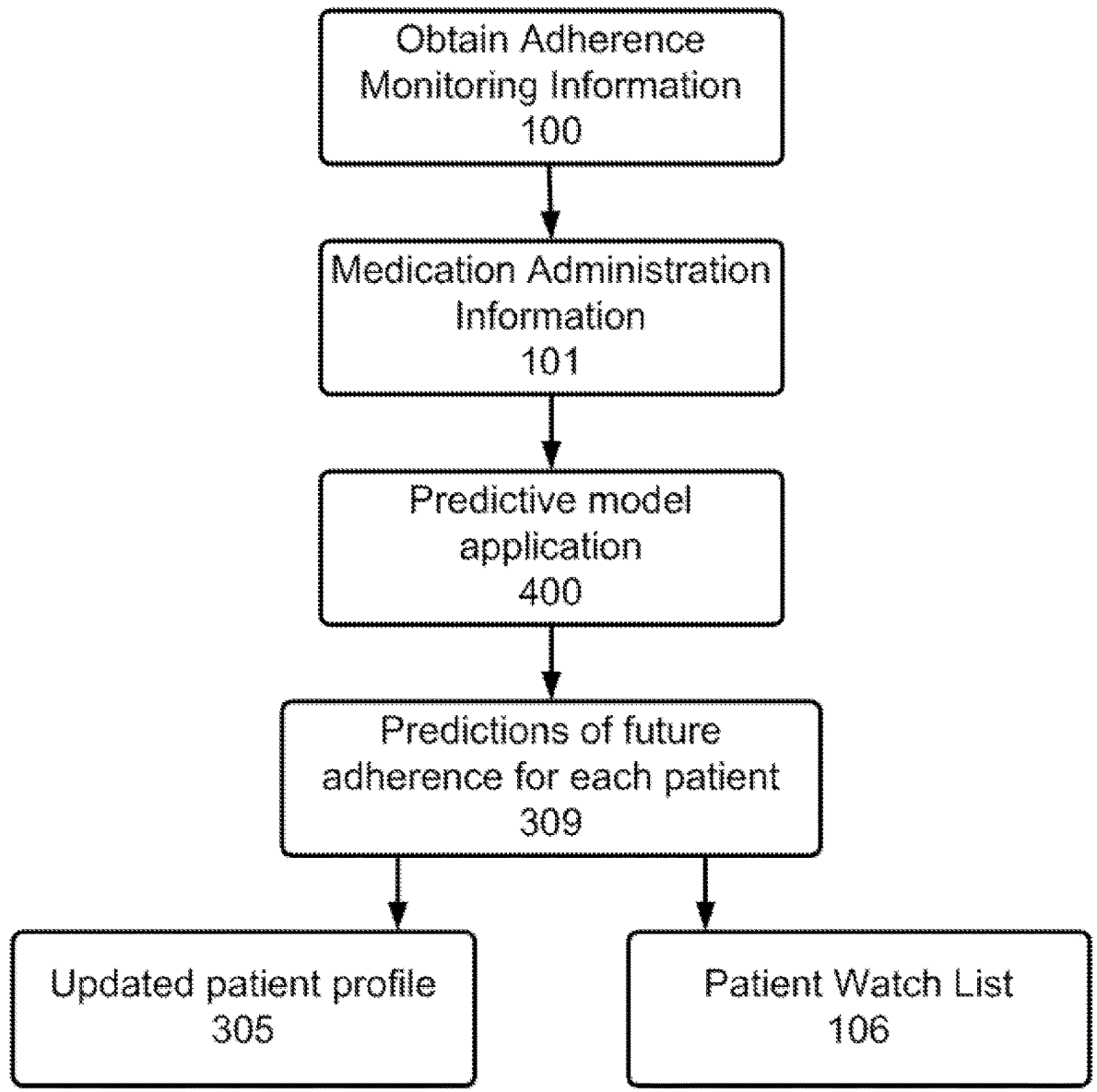
FIG. 4 is a flowchart depicting a method for creating a watch list for potential proactive interaction in accordance with an embodiment of the invention.

FIG. 4 next shows a method for identifying patients for potential proactive intervention, thus providing detail related to the implementation of step 104 from FIG. 1. Using the medication administration information 101 and other data captured from one or more patient medication adherence monitoring devices at step 100, processing in accordance with step 104 of FIG. 1 allows a way to find a group of patients within a population who are at increased risk of non-adherence. As is further shown in FIG. 4, patient data is fed into a predictive model at step 400, which preferably makes predictions at step 309 for each patient's adherence over some predetermined future time period, say k days. Any patient whose adherence rate is predicted to be below a predetermined rate of x % over the following k days may be considered at risk and preferably added to the watch list 106. For example, suppose k=7 and x=80. Each patient who is predicted to take fewer than 80% of his or her doses over the next week may be added to the watch list. The predictions for all patients—not just those added to the watch list—may preferably be integrated into the updated patient profile 106.

As noted above, a decision about whether, when, and how to intervene is preferably made by using the patient watch list 106 in conjunction with one or more updated patient profiles 305. Since the system makes adherence predictions for each dose each patient is scheduled to take over the following k days, it is possible to target a proactive intervention to the day (or any number of days or other desired time period) before a patient is predicted to miss a dose. The following table is an example of the output 309 of the predictive model 400 for one exemplary patient's data. Suppose k=7 and x=80% adherence. The predicted adherence of this patient to a daily dose of medication for each of the following seven days, based upon an exemplary predictive model, may be indicated in Table A. A "1" in the "adherence" row indicates that the daily dose is predicted to be taken, a "0" that the dose is predicted to be missed.

TABLE A

| Day | 1 | 2 | 3 | 4 | 5 | 6 | 7 |
|---|---|---|---|---|---|---|---|
| Adherence | 1 | 1 | 1 | 0 | 1 | 0 | 1 |

The predicted adherence rate for this patient over the next seven days is 71%, and so this patient would preferably be added to the watch list 106. A proactive intervention may then be tentatively scheduled to be provided on day three, anticipating the missed dose on day four. However, if a dose is actually missed earlier than day four, the patient may alternatively receive an automatic retrospective intervention upon the first missed dose.

Criteria other than the adherence rate may also be chosen for inclusion of a patient on the watch list. For example, placement of a patient on the watch list may result if a gap in adherence of m consecutive days was predicted. Here m is greater than or equal to zero and less than or equal to k.

Instead of binary predictions about adherence, as in Table A above, the predictions of future adherence may take the form of probabilities that each dose over the next k days will be missed. This may preferably allow for pre-emptive intervention prior to doses with particularly high probabilities of being missed. The following table gives an example, which represents the output of the predictive model for a single patient. Suppose k=7 and x=80%, and that for this patient the probabilities of missing a daily dose of medication for each of the next seven days are as given in Table B, below. From these probabilities, it is possible to compute an expected adherence rate for the next seven days, which is equal to 65%. Thus, this patient may preferably be assigned to the watch list. However, the probability of a missed dose is relatively low until day five. A proactive intervention could then be targeted to take place on day four or earlier, as desired. Various embodiments of the invention may also take into account weekend schedules, times of day, etc. for determining one or more trends to be followed for one or more patients.

TABLE B

| Day | 1 | 2 | 3 | 4 | 5 | 6 | 7 |
|---|---|---|---|---|---|---|---|
| Probability of missed dose | .10 | .25 | .20 | .10 | .55 | .75 | .50 |

It should be noted that nothing precludes setting k=1 and x=100. In this case, the watch list consists of patients who are predicted to not take all of their next day's medication. A proactive intervention could then be arranged for each patient on this watch list, for each patient whose overall adherence level is below some threshold, or for each patient who meets some other criteria.

Additional situations may be employed, such as predicting a patient's adherence rate for an entire clinical trial based on a few weeks of data. It may be possible to remove one or more patients from the clinical trial with predicted adherence below a certain level. Additionally, the system and method may be employed to predict whether population-wide adherence will be above or below a certain level at some future time. Further review of photos, video audio and other collected data may allow for further insight in to the patient scores and profiles to allow for further identification of normal use, usability issues, intentional or non-intentional non-adherence, and whether the patient should be placed in the watchlist. Thus, broadcasting of information to aid adherence may be employed.

The predictive model 400 may be created from known methods from statistics, machine learning, data mining, and related fields. Since the data are collected at regular time intervals, they form one or more time series. Known models from time series analysis thus may be used to make predictions about future adherence. If time series models are used, the only data required are a patient's past data. Sample data from other members of the population, or from similar existing or past populations aren't required, but may be employed as desired. In addition, a model may be fitted to each patient's data. Since different patients may have different behavioral patterns, this is an advantage to time series models. In this case, the predictive model 400 may preferably comprise an aggregate of predictive models for each patient.

Supervised learning methods from machine learning may also be employed. These methods require a set of training data that ideally will come from a similar population. A model may then be fit to the training data. With this approach, this model is preferably applied to each of the patients.

Another approach may be to first use unsupervised learning methods, or cluster analysis, on a set of training data to group patients into some number of predetermined groups, and then use supervised learning methods to fit a model to each of the groups. On the population data, then, first each patient is assigned to one of the groups, and then adherence predictions are made using the model for that group. In this case, the predictive model 400 may comprise a collection of the predictive models for each group created via the cluster analysis.

Whatever methods are used to create the predictive model, the model may be updated regularly to take into account changes in longer-term patient behavior, including the effect that both proactive and retrospective interventions are having on patients.

The same type of reasoning noted above may be used to create a variation on that module, where instead of adherence—or in addition to it—predictions may be made about how late a patient may be in taking each dose over some future time period. This may be useful in case the medication is one such that timing is crucial for insuring effectiveness. In the same way as described above, a watch list could be created and certain doses for each patient could be targeted for proactive intervention. Multiple medications may also be profiled in the patient score, each receiving a separate score, or two or more medications sharing such a score.

While the system has been described related to medication adherence, the system may be applied to any other type of data in which performance is measured over time, and a predictive model may be valuable to determine how to interact with an actor.

Therefore in accordance with one or more embodiments of the invention, medication adherence information may be accumulated, predictive algorithms may be employed to predict future non-adherence, and thus predictive intervention may be provided. Such intervention is designed to improve future medication adherence of a patient or population.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A system for predictively intervening with a user to improve medication adherence, the system comprising:
   a display;
   a video capture device;
   one or more processors; and
   one or more non-transitory, computer-readable storage media storing instructions that, when executed by the one or more processors, cause the one or more processors to perform operations comprising:
   obtaining a set of training data associated with a group of patients;
   splitting the group of patients into a plurality of sub-groups using unsupervised learning or cluster analysis;
   training a corresponding machine learning model for each sub-group of the plurality of sub-groups based on training data of patients included in the sub-group;
   outputting, to the display, one or more instructions related to proper medication administration;
   obtaining one or more video sequences of the user administering medication in accordance with the one or more instructions, the one or more video sequences captured by the video capture device;
   determining that the user in the one or more video sequences does not properly administer the medication;
   based on determining that the user does not properly administer the medication, outputting, to the display, additional instructions to the user in near-real time;
   assigning the user to a first sub-group of the plurality of sub-groups based on a similarity of the user to patients included in the first sub-group;
   inputting data of the user, including a determination that the user did not properly administer the medication in response to the one or more instructions, into a first machine learning model corresponding to the first sub-group;
   obtaining, as an output of the first machine learning model, for each future day of a plurality of future days, a corresponding prediction of whether the user will properly administer the medication on the future day, wherein, for at least one future day of the plurality of future days, the corresponding prediction indicates that the user will not properly administer the medication, and wherein, for at least one other future day of the plurality of future days, the corresponding prediction indicates that the user will properly administer the medication;
   selecting a future time point that is prior to the at least one future day where the corresponding prediction indicates that the user will not properly administer the medication; and
   at the future time point, outputting, to the display, additional information, wherein the additional information comprises an encouragement to improve medication adherence.

2. The system of claim 1, wherein, for each future day of the plurality of future days, the prediction of whether the user will properly administer the medication on the future day comprises a binary determination of whether the user is predicted to properly administer the medication on the future day.

3. The system of claim 1, wherein, for each future day of the plurality of future days, the prediction of whether the user will properly administer the medication on the future day comprises a predicted probability that the user properly administers the medication on the future day.

4. The system of claim 1, wherein the output of the first machine learning model comprises a predicted lateness of the user in properly administering a dose of the medication.

5. The system of claim 1, wherein the operations comprise:
determining a plurality of category scores for the user, each category score indicating behavior of the user in a respective category of behavior; and
determining a plurality of weighted combinations of the plurality of category scores, each weighted combination being based on a different weighting of the plurality of category scores,
wherein each weighted combination indicates past user medication adherence or future user medication adherence.

6. The system of claim 5, wherein the operations comprise:
providing one or more weighted combinations of the plurality of weighted combinations to one or more different healthcare providers selected from the group of: nurse, doctor, family member, insurance company, hospital, and health system, wherein each weighted combination emphasizes a different aspect of user behavior.

7. The system of claim 5, wherein the operations comprise:
determining a first weighted combination of the plurality of weighted combinations that best fits historical medication administration data of the user.

8. The system of claim 1, wherein the operations comprise:
selecting, based on one or more of a disease state of the user, a population type of the first sub-group, socio-economic data of the user, or historical data, the future time point as a time point at which a reminder to the user is predicted to be more effective compared to other possible future reminder times.

9. A method for intervening with a user to improve medication adherence in accordance with a medication adherence monitoring apparatus comprising
a display; and
a video capture device, the method comprising:
obtaining a set of training data associated with a group of patients;
splitting the group of patients into a plurality of sub-groups using unsupervised learning or cluster analysis;
training a corresponding machine learning model for each sub-group of the plurality of sub-groups based on training data of patients included in the sub-group;
providing, via the display, one or more instructions related to proper medication administration at a predetermined medication administration time;
obtaining one or more video sequences of the user administering medication in accordance with the one or more instructions, the one or more video sequences captured by the video capture device;
determining that the user in the one or more video sequences does not properly administer the medication in response to the one or more instructions;
based on determining that the user does not properly administer the medication, providing additional instructions to the user in near-real time via the display;
assigning the user to a first sub-group of the plurality of sub-groups based on a similarity of the user to patients included in the first sub-group;
inputting data of the user, including a determination that the user did not properly administer the medication in response to the one or more instructions, into a first machine learning model corresponding to the first sub-group;
obtaining, as an output of the first machine learning model, for each future day of a plurality of future days, a corresponding prediction of whether the user will properly administer the medication on the future day, wherein, for at least one future day of the plurality of future days, the corresponding prediction indicates that the user will not properly administer the medication, and wherein, for at least one other future day of the plurality of future days, the corresponding prediction indicates that the user will properly administer the medication;
selecting a future time point that is prior to the at least one future day where the corresponding prediction indicates that the user will not properly administer the medication; and
at the future time point, outputting, to the display, additional information, wherein the additional information comprises an encouragement to improve medication adherence.

10. The method of claim 9, wherein, for each future day of the plurality of future days, the prediction of whether the user will properly administer the medication on the future day comprises a binary determination of whether the user is predicted to properly administer the medication on the future day.

11. The method of claim 9, for each future day of the plurality of future days, the prediction of whether the user will properly administer the medication on the future day comprises a predicted probability that the user properly administers the medication on the future day.

12. The method of claim 9, wherein the output of the first machine learning model comprises a predicted lateness of the user in properly administering a dose of the medication.

13. The method of claim 9, comprising:
determining a plurality of category scores for the user, each category score indicating behavior of the user in a respective category of behavior; and
determining a plurality of weighted combinations of the plurality of category scores, each weighted combination being based on a different weighting of the plurality of category scores,
wherein each weighted combination indicates past user medication adherence or future user medication adherence.

14. The method of claim 13, comprising:
providing one or more weighted combinations of the plurality of weighted combinations to one or more different healthcare providers selected from the group of: nurse, doctor, family member, insurance company, hospital, and health system, wherein each weighted combination emphasizes a different aspect of user behavior.

15. The method of claim 13, comprising ranking the user relative to other users based on a first weighted combination of the plurality of weighted combinations.

16. The method of claim 15, comprising employing a rank of the user to allocate resources for medication adherence intervention.

17. The method of claim 13, comprising:
determining a first weighted combination of the plurality of weighted combinations that best fits historical medication administration data of the user.

18. One or more non-transitory, computer-readable media storing instructions that, when executed by one or more processors, cause the one or more processors to perform operations comprising:
- obtaining a set of training data associated with a group of patients;
- splitting the group of patients into a plurality of sub-groups using unsupervised learning or cluster analysis;
- training a corresponding machine learning model for each sub-group of the plurality of sub-groups based on training data of patients included in the sub-group;
- outputting, to a display, one or more instructions related to proper medication administration;
- obtaining one or more video sequences of a user administering medication in accordance with the one or more instructions;
- determining that the user in the one or more video sequences does not properly administer the medication;
- based on determining that the user does not properly administer the medication, outputting, to the display, additional instructions to the user in near-real time;
- assigning the user to a first sub-group of the plurality of sub-groups based on a similarity of the user to patients included in the first sub-group;
- inputting data of the user, including a determination that the user did not properly administer the medication in response to the one or more instructions, into a first machine learning model corresponding to the first sub-group;
- obtaining, as an output of the first machine learning model, for each future day of a plurality of future days, a corresponding prediction of whether the user will properly administer the medication on the future day, wherein, for at least one future day of the plurality of future days, the corresponding prediction indicates that the user will not properly administer the medication, and wherein, for at least one other future day of the plurality of future days, the corresponding prediction indicates that the user will properly administer the medication;
- selecting a future time point that is prior to the at least one future day where the corresponding prediction indicates that the user will not properly administer the medication; and
- at the future time point, outputting, to the display, additional information, wherein the additional information comprises an encouragement to improve medication adherence.

* * * * *

UNITED STATES PATENT AND TRADEMARK OFFICE
CERTIFICATE OF CORRECTION

PATENT NO. : 11,631,484 B1
APPLICATION NO. : 14/517468
DATED : April 18, 2023
INVENTOR(S) : Hanina et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1255 days.

Signed and Sealed this
Sixteenth Day of April, 2024

Katherine Kelly Vidal
*Director of the United States Patent and Trademark Office*